United States Patent
Jia et al.

(10) Patent No.: US 10,065,022 B2
(45) Date of Patent: Sep. 4, 2018

(54) INTRAVASCULAR INTERVENTIONAL TACTILE PROBE HAVING TOUCHING FORCE RANGE AND POSITION INFORMATION FEEDBACK

(71) Applicant: SHANGHAI CADENZA MEDICAL TECHNOLOGY CO., LTD., Shanghai (CN)

(72) Inventors: Luoqi Jia, Shanghai (CN); Zongyi Jia, Shanghai (CN)

(73) Assignee: Shanghai Cadenza Medical Technology Co., Ltd., Shanghai (CN)

( * ) Notice: Subject to any disclaimer, the term of this patent is extended or adjusted under 35 U.S.C. 154(b) by 168 days.

(21) Appl. No.: 15/128,758

(22) PCT Filed: Mar. 13, 2015

(86) PCT No.: PCT/CN2015/074146
§ 371 (c)(1),
(2) Date: Sep. 23, 2016

(87) PCT Pub. No.: WO2015/143998
PCT Pub. Date: Oct. 1, 2015

(65) Prior Publication Data
US 2017/0106169 A1    Apr. 20, 2017

(30) Foreign Application Priority Data

Mar. 28, 2014  (CN) .......................... 2014 1 0123074

(51) Int. Cl.
*A61M 25/00* (2006.01)
*A61M 25/01* (2006.01)
(Continued)

(52) U.S. Cl.
CPC ......... *A61M 25/0105* (2013.01); *A61B 5/746* (2013.01); *A61B 5/7455* (2013.01);
(Continued)

(58) Field of Classification Search
CPC .. A61M 25/0105; A61B 90/06; A61B 5/7455; A61B 5/746; A61N 1/05
(Continued)

(56) References Cited

U.S. PATENT DOCUMENTS 6,011,391 A * 1/2000 Nix ........................ G01B 7/105
324/230
2009/0138007 A1* 5/2009 Govari ................. A61B 1/0008
606/33

FOREIGN PATENT DOCUMENTS

CN    101589972 A    12/2009
CN    201558168 U     8/2010
(Continued)

*Primary Examiner* — Phillip Gray
(74) *Attorney, Agent, or Firm* — Muncy, Geissler, Olds & Lowe, P.C.

(57) ABSTRACT

A tactile probe for endovascular intervention with feedbacks informative of the range and direction of a contact force includes: a central column (7); a plurality of lateral electrodes (2) around the central column (7); a conductive contact sleeve (1) that is axially and radially movable relative to the central column (7); a top electrode (3) in movable connection with the central column (7); and an alert electrode (4) configured to generate: a lateral contact signal, upon the contact sleeve (1) radially moving relative to the central column (7) and being electrically connected to at least one lateral electrode (2); a top contact signal, upon the contact sleeve (1) axially moving relative to the central column (7) a first distance (d1) and being electrically connected to the top electrode (3); and a warning signal, upon the contact sleeve (1) axially moving relative to the central column (7) a second distance (d2) and being electrically connected to the alert electrode (4). The tactile probe can identify the direction of the contact force and also indicate its magnitude.

20 Claims, 10 Drawing Sheets

(51) Int. Cl.
  *A61B 5/00*   (2006.01)
  *A61B 90/00*  (2016.01)
  *A61N 1/05*   (2006.01)
  *A61N 1/36*   (2006.01)
(52) U.S. Cl.
  CPC .............. *A61B 90/06* (2016.02); *A61N 1/05* (2013.01); *A61N 1/36* (2013.01); *A61B 2090/065* (2016.02); *A61M 2025/0166* (2013.01)
(58) Field of Classification Search
  USPC ......................................................... 604/528
  See application file for complete search history.

(56) References Cited

FOREIGN PATENT DOCUMENTS

| | | |
|---|---|---|
| CN | 103041495 A | 4/2013 |
| CN | 103877664 A | 6/2014 |
| CN | 203790417 U | 8/2014 |

\* cited by examiner

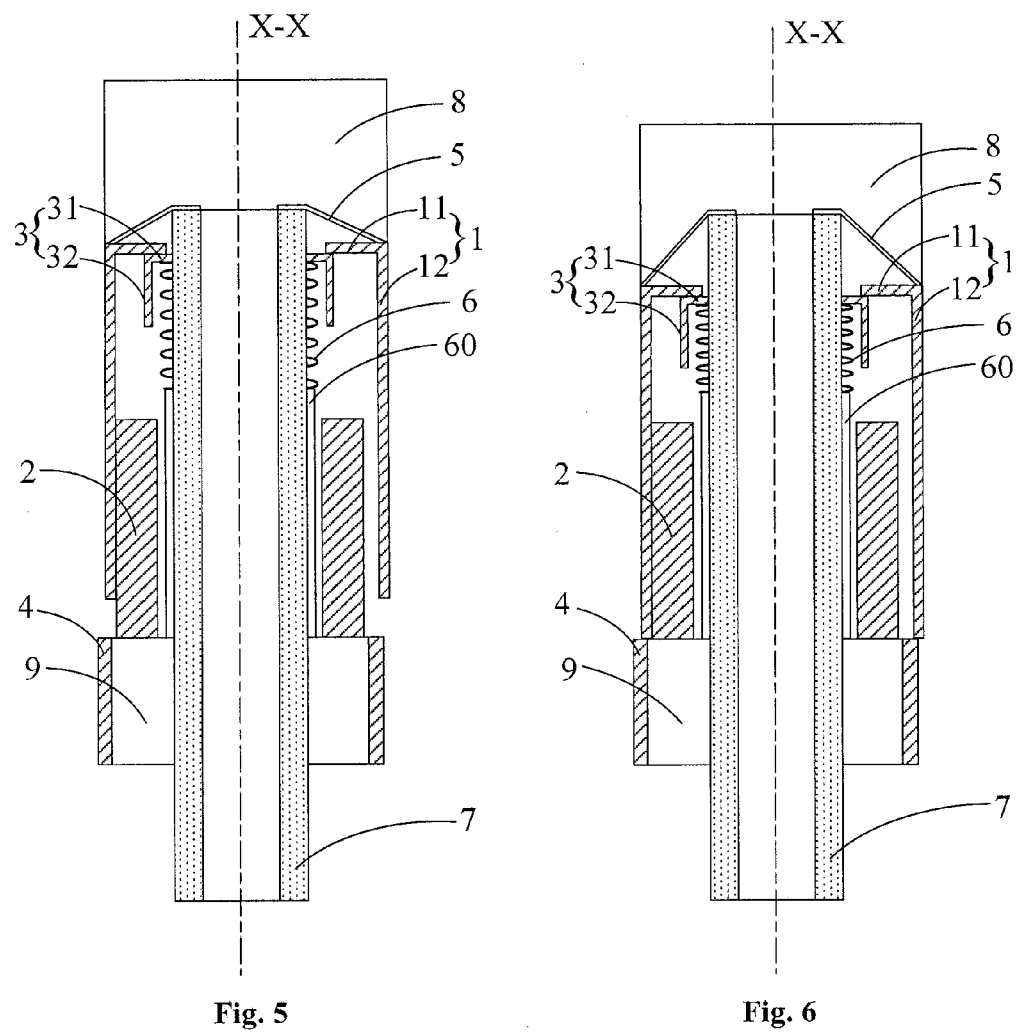

INTRAVASCULAR INTERVENTIONAL TACTILE PROBE HAVING TOUCHING FORCE RANGE AND POSITION INFORMATION FEEDBACK

TECHNICAL FIELD

The present invention relates to the field of medical devices and, in particular, to tactile probes for endovascular intervention with feedbacks informative of the range and direction of a contact force.

BACKGROUND

The development of endovascular intervention is a big leap in the history of the human medical science. However, currently, the insertion of a guide catheter for endovascular intervention has to be conducted in a "blind" way relying on the operator's hand tactility and experience. As a result, blood vessel wall injuries are often caused, or even worse, ruptures of blood vessel occur, which may lead to significant accidents such as massive bleeding. For this reason, there is a need in this art to develop an interventional catheter with sensing abilities for clinical use which can prevent blood vessel wall injuries.

Publication No. CN103041495A filed by the applicant of the present invention discloses the invention of a tactile probe for endovascular intervention using sensors with electrode-based switches to detect in which one(s) of seventeen possible directions the probe comes into contact with a blood vessel wall. It solves the problems arising from use of the conventional blind insertion method, i.e., inability to accurately detect a contact of the interventional catheter with a blood vessel wall and inability to identify the direction in which the contact occurs.

Nevertheless, during practical use of the tactile probe, it was found that, while the probe could indicate the direction in which the catheter comes into contact with the blood vessel wall, the magnitude of the contact force remained unknown. In practical use, it was often the case that, upon the interventional catheter coming into contact with an obstacle in a blood vessel such as a physiological or pathological narrow site, although the interventional procedure would have been continued without hurting the vascular wall by slightly increasing the contact force, as the probe could only detect the presence of the obstacle but could not tell if it could pass through the obstacle with a slight increase in the force, the continuation of the procedure had to be given up.

In view of this, there is a need for an improved tactile probe for endovascular intervention which can detect both the direction and magnitude of the contact force.

SUMMARY OF THE INVENTION

The problem to be solved by this invention is therefore to provide such a tactile probe for use with a catheter for endovascular intervention which can not only identify the direction in which a contact occurs but also indicate how strong the contact is.

In order to solve the above problem, in a first aspect of the invention, there is provided a tactile probe, including: an axially extending central column; a plurality of lateral electrodes evenly distributed around the central column; a conductive contact sleeve circumferentially surrounding the central column, the contact sleeve including a top portion and a side wall, the top portion connected by an elastomer to a leading end of the central column, the side wall having a first end in connection with the top portion and a second end circumferentially surrounding the plurality of lateral electrodes, the side wall spaced apart from each of the plurality of lateral electrodes by a radial gap; a top electrode connected to the central column and spaced from the top portion of the contact sleeve by a first axial distance; and an alert electrode fixed to the central column and positioned behind both the contact sleeve and the top electrode, wherein the contact sleeve is radially movable relative to the central column and is able to be electrically connected to at least one of the plurality of lateral electrodes to allow a lateral contact signal to be generated, and wherein the contact sleeve is axially movable relative to the central column such that in an event of the contact sleeve being axially displaced relative to the central column by the first axial distance, an electrical connection is established between the contact sleeve and the top electrode to generate a top contact signal, and in an event of the contact sleeve being axially displaced relative to the central column by a second axial distance that is greater than the first axial distance, an electrical connection is established between the contact sleeve and the alert electrode to generate a warning signal.

In order to solve the above problem, in a second aspect of the invention, there is provided a tactile probe, including: an axially extending central column; a plurality of lateral electrodes evenly distributed around the central column; a substantially annular, conductive contact sleeve circumferentially surrounding the central column, the contact sleeve having a first end in connection with a leading end of the central column via an elastomer and a second end circumferentially surrounding the plurality of lateral electrodes, the contact sleeve spaced apart from each of the plurality of lateral electrodes by a radial gap; a top electrode connected to the central column and spaced from the second end of the contact sleeve by a first axial distance; and an alert electrode fixed to the central column and positioned behind both the contact sleeve and the top electrode, wherein the contact sleeve is radially movable relative to the central column and is able to be electrically connected to at least one of the plurality of lateral electrodes to allow a lateral contact signal to be generated, and wherein the contact sleeve is axially movable relative to the central column such that in an event of the contact sleeve being axially displaced relative to the central column by the first axial distance, an electrical connection is established between the contact sleeve and the top electrode to generate a top contact signal, and in an event of the contact sleeve being axially displaced relative to the central column by a second axial distance that is greater than the first axial distance, an electrical connection is established between the contact sleeve and the alert electrode to generate a warning signal.

Upon a tactile probe according to the present invention coming into contact with an obstacle, the contact sleeve may be brought into contact with one or more of the top electrode and the plurality of lateral electrodes, thereby resulting in a signal which can accurately indicate the direction in which the probe came into contact with the obstacle. This can help the operator to move the interventional catheter opposite to the obstacle and hence easily get rid of or circumvent the obstacle to continue advancing the catheter. In addition, the threshold alert electrode allows detection of the magnitude of the contact force. When the probe produces a first resistance signal (i.e., a top contact signal) which indicates that there is an obstacle directly or obliquely ahead, it can be known that the resistance is still within a controlled range and the catheter can be further advanced. However, if the probe produces a second signal (i.e., a warning signal), it is indicated that the resistance has reached a threshold, and further advancement of the catheter will cause a damage to the blood vessel wall and should be stopped.

Further, the tactile probes combine ingenious design, inexpensive materials and simple fabrication processes and can therefore be manufactured at low cost to meet the requirements on disposable consumables for use in endovascular intervention.

BRIEF DESCRIPTION OF THE DRAWINGS

FIGS. 1 to 6 are schematic cross-sectional views illustrating a tactile probe according to a first embodiment of the present invention.

DETAILED DESCRIPTION

The forgoing objects, features and advantages of the present invention will become apparent from the following detailed description of a few illustrative embodiments thereof, which is to be read in connection with the accompanying drawings. Note that these drawings are provided in a very simplified form not necessarily presented to scale, with the only intention of facilitating convenience and clarity in explanation.

According to clinical practice in endovascular intervention procedures, vascular wall injuries occurring during endovascular insertion of catheters are mainly caused by directly or obliquely forward pushing forces exerted by the catheters. On the other hand, since a vascular wall is somehow elastic, a push force controlled within an appropriate range will not lead to any injury or only cause a minimal damage to the vascular wall. In view of this, the core concept of this invention is to modify a tactile probe designed as a leading portion of an interventional catheter so as to allow the probe to indicate the magnitude of a pressure exerted by an object straight or obliquely ahead of the probe, i.e., a pushing force from a blood vessel wall or an obstacle in front of, or laterally in front of, the probe, such that it is determinable whether the force is within a controlled range, thereby facilitating advancement of the catheter within the blood vessel and effectively preventing the catheter from injuring the vascular wall.

Embodiment 1

Figure 1:
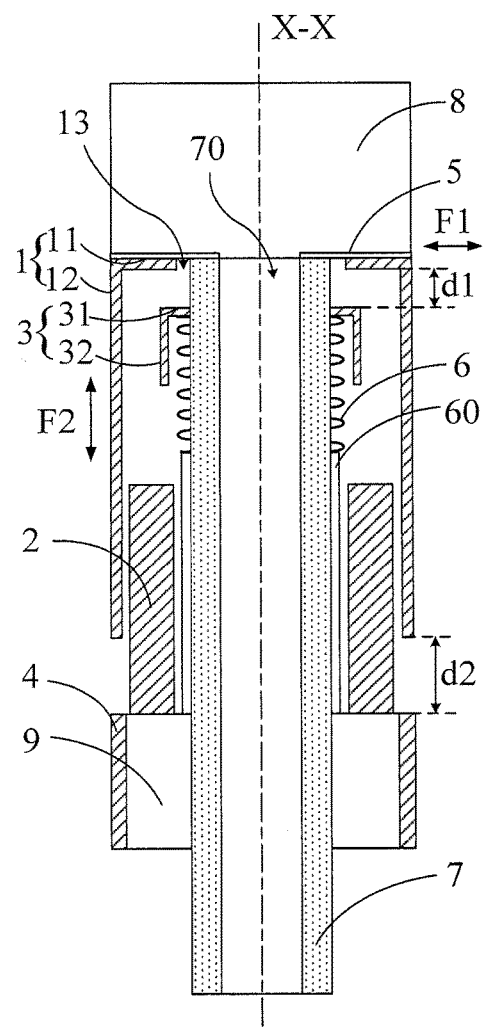
Figure 2:
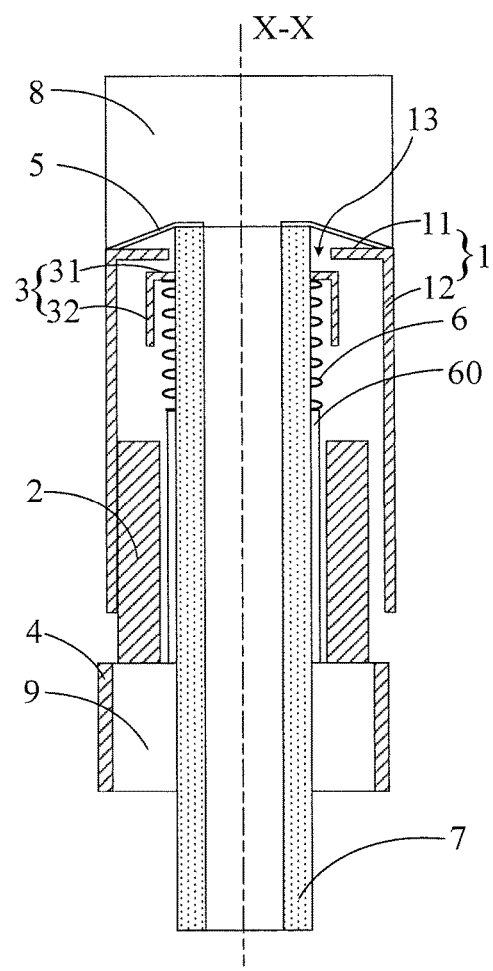

FIG. 1 is a cross-sectional view of a tactile probe according to a first embodiment of the present invention. The tactile probe is implemented as a foremost portion of a catheter for endovascular intervention. As shown in FIG. 1, the tactile probe includes a central column 7 extending along a longitudinal axis X-X. A leading end of the central column 7 is connected by a polymeric elastomer 5 to a conductive contact sleeve 1 which may be formed, for example, by an annular metal part that allows current to flow therein. In particular, the contact sleeve 1 includes a top portion 11 and an annular side wall 12. The top portion 11 is essentially a disk with a central opening 13 which allows the contact sleeve to be disposed over the central column 7. The opening 13 has a diameter that is greater than an outer diameter of the central column 7, leaving a space for radial movement of the contact sleeve 1 relative to the central column 7. The top portion 11 and the side wall 12, of the contact sleeve 1, may be fabricated separately and then connected together, or integrally molded into one piece. The polymeric elastomer 5 may be an elastic film with its central portion fixed to the leading end of the central column 7 and its peripheral part fixed to the top portion 11 of the contact sleeve 1. The elasticity of the polymeric elastomer 5 enables the contact sleeve 1 to move both axially along the axis X-X (as indicated by the arrow F2) and radially (as indicated by the arrow F1) with respect to the central column 7. FIG. 2 shows the contact sleeve 1 after it has moved a distance both axially and radially. The contact sleeve 1 serves as a signal input device for the entire tactile probe and is coupled to an electrical signal input terminal via a wire (not shown).

Figure 7:
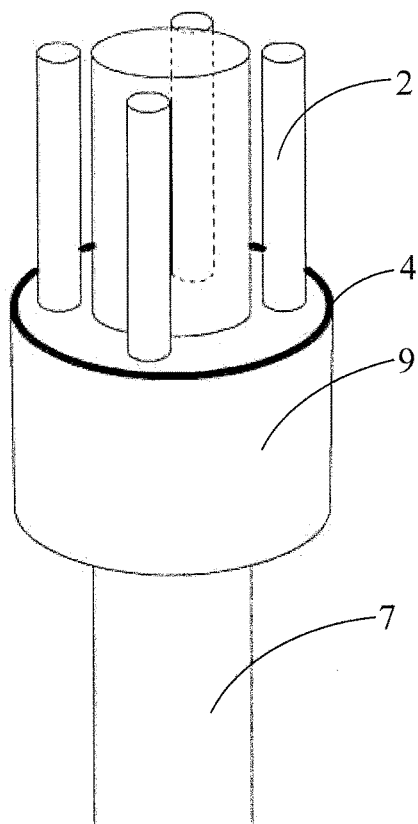
FIG. 7 schematically shows the distribution of lateral electrodes according to the first embodiment of the present invention.

As shown in FIG. 1, the tactile probe further includes a plurality of lateral electrodes 2 evenly distributed around the central column 7. The plurality of lateral electrodes 2 are all disposed on a leading surface of a lateral-electrode base 9, namely, the surface of the base 9 facing toward the leading end of the central column 7, and are secured to the central column 7 through the lateral-electrode base 9. Each of the lateral electrodes 2 may resemble a pillar, a sheet, a dot or a spike. In this embodiment, with four lateral electrodes as an example, FIG. 7 shows the lateral electrodes 2 arranged around the central column 7. As illustrated in FIG. 7, the four lateral electrodes 2 are equidistantly arranged on a circle. Each of the lateral electrodes 2 acts as a contact direction signal generator and is connected to a respective electrical signal output terminal via a wire (not shown), so as to work with the contact sleeve 1 to output a signal indicative of the probe laterally coming into contact with an obstacle.

With continued reference to FIG. 1, the trailing end of the side wall 12 of the contact sleeve 1 circumferentially surrounds the plurality of lateral electrodes 2 and the side wall 12 is spaced from each of the lateral electrodes 2 by a radial gap. A contact pressure is created when the contact sleeve 1 laterally comes into contact with an obstacle, under the effect of which, the contact sleeve 1 is pushed and displaced radially relative to the central column 7 in the direction of the contact. This decreases the gap(s) between the contact sleeve 1 and one or two of the lateral electrodes 2, until the one or two of the lateral electrodes 2 come(s) into contact with the side wall 12 of the contact sleeve, thereby closing the corresponding circuit(s). FIG. 2 shows the side wall 12 of the contact sleeve in contact with one of the lateral electrodes 2. By detecting signal(s) output from the one or two of the lateral electrodes 2 contacting the contact sleeve 1, the lateral direction of the obstacle with respect to the contact sleeve 1 can be known. Adjusting the radial gaps of the lateral electrodes 2 with respect to the side wall 12 of the contact sleeve 1 allows changing the magnitude of the force under which the probe can sense a contact of the side wall. Although four lateral electrodes are used in this embodiment, the number of the lateral electrodes is not so limited. It will be readily appreciated that the greater the number of the lateral electrodes, the more precise the sensed lateral contact direction.

With continued reference to FIG. 1, the tactile probe further includes a top electrode 3 and a threshold alert electrode 4. The top electrode 3 encompasses the circumference of the central column 7 and is located axially between the lateral electrodes 2 and the top portion 11 of the contact sleeve 1. The top electrode is connected to the central column 7 through a spring 6 and can move longitudinally along the axis X-X with respect to the central column 7. One end of the spring 6 is fixed to the top electrode 3, and the other end may either be directly, or indirectly through a spring seat 60, secured to the central column 7. The spring seat 60 may be a rigid ring-shaped component disposed over the central column 7 with one end abutting against the leading surface of the lateral-electrode base 9 and the other end for fixation of the spring 6. The threshold alert electrode 4 is a metallic, sleeve-like electrode disposed over the circumference of the lateral-electrode base 9. It is spaced apart from the lateral electrodes 2 and is axially aligned with the side wall 12 of the contact sleeve 1. In addition, the threshold alert electrode 4 is positionally fixed relative to the central column 7. With similarity to the lateral electrodes 2, both of the top electrode 3 and the threshold alert electrode 4 are connected to respective electrical signal output terminals by wires (not shown), in order to work with the contact sleeve 1 to output a signal indicating the probe coming into contact with a straight-ahead obstacle and a signal indicating a directly or obliquely forward pushing force exerted by the interventional catheter on a blood vessel wall having reached a threshold, respectively.

The top electrode 3 has a leading surface 31 facing straight forward, i.e., toward the top portion 11 of the contact sleeve, and can be formed by, for example, a metal sheet. Optionally, the top electrode 3 may additionally include an annular support 32 which is connected to the periphery of the leading surface 31, in order to support the top electrode 3 and thus prevent the top electrode from undergoing significant deformation under an external force.

Figures 3, 4:
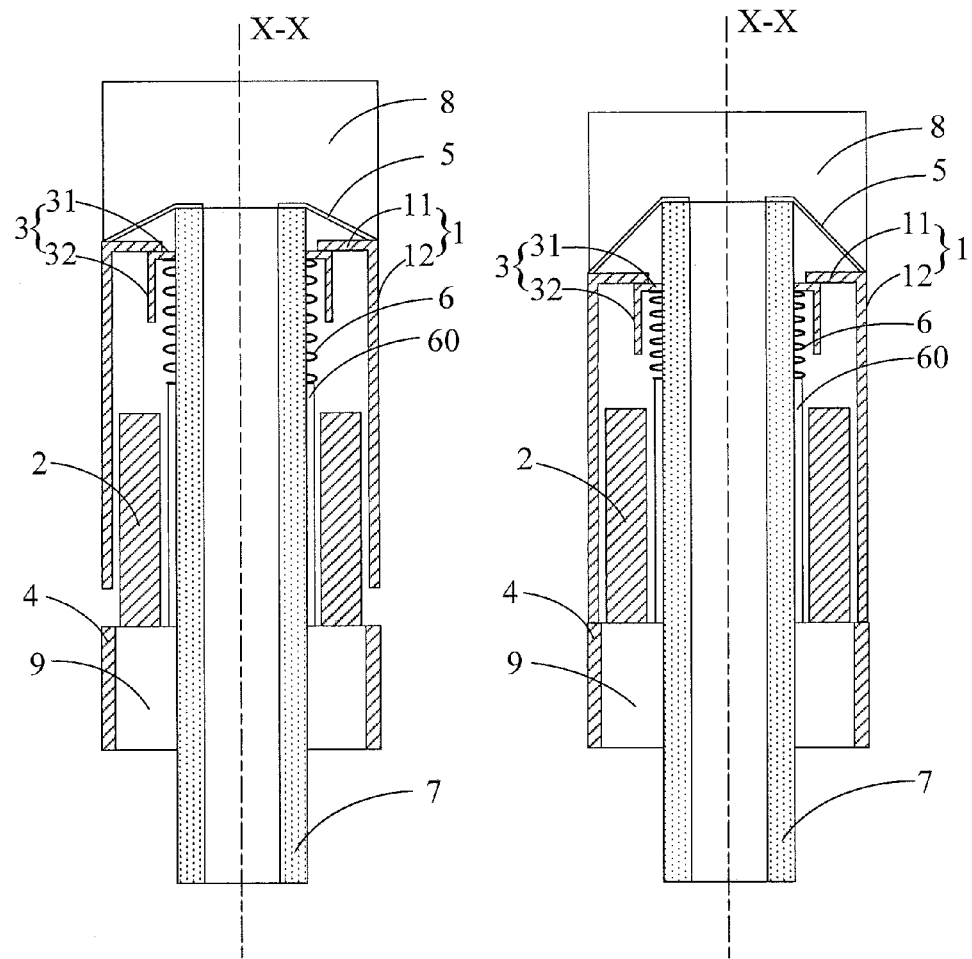

In an initially configuration in which the contact sleeve 1 is not subject to any external force, the axial distance from the leading surface 31 of the top electrode 3 to the top portion 11 of the contact sleeve is d1, and the axial distance from the threshold alert electrode 4 to the side wall 12 of the contact sleeve is d2. In case of the contact sleeve 1 coming into contact with an obstacle straight ahead of it, the contact sleeve 1 will move backward along the axis X-X, i.e., toward the top electrode 3, under the effect of a force exerted by the obstacle. Upon it having moved a distance of d1, as shown in FIG. 3, the top portion 11 of the contact sleeve comes into contact with the leading surface 31 of the top electrode 3, closing a circuit which causes the top electrode 3 to output a signal indicative of the touch. If the contact sleeve 1 continues moving backward along the axis X-X under the force from the obstacle directly ahead of it, the top portion 11 of the contact sleeve 1 will impose a backward force on the top electrode 3 so that the spring 6 will be compressed and hence drive the top electrode 3 to also move backward. Upon it having moved a distance of d2, as shown in FIG. 4, the side wall 12 of the contact sleeve will come into contact with the threshold alert electrode 4, thereby closing a circuit which causes the threshold alert electrode 4 to output a warning signal indicating that the probe is being subject to a threshold pressure and further advancing of the interventional catheter should be stopped.

While the probe has been illustrated in FIGS. 3 and 4 as moving backward under a pressure from straight ahead, it will be readily appreciated by those skilled in the art that a pressure from obliquely ahead acting on the probe that consists of an axial component and a radial component will drive also radial movement of the contact sleeve 1 in addition to its backward movement along the axis X-X, so that when it radially comes into contact with one or two of the lateral electrodes 2, the lateral electrode(s) will further generate signal(s) indicative of the lateral contacting. FIGS. 5 and 6 show, under the effect of a pressure from left ahead, the contact sleeve 1 coming into contact with the top electrode 3 and the lateral electrode(s) 2 and the contact sleeve 1 coming into contact with the top electrode 3, the lateral electrode(s) 2 and the threshold alert electrode 4, respectively.

Thus, in the case of the four lateral electrodes, when assuming the four lateral electrodes represent the respective four directions: east, south, west and north, the tactile probe can provide twenty-six distinct signals that indicate ahead, east, south, west, north, southeast, northeast, southwest, northwest, east ahead, south ahead, west ahead, north ahead, southeast ahead, northeast ahead, southwest ahead, northwest ahead, threshold ahead, threshold east ahead, threshold south ahead, threshold west ahead, threshold north ahead, threshold southeast ahead, threshold northeast ahead, threshold southwest ahead, threshold and northwest ahead. An increase in the number of the lateral electrodes will lead to a greater number of possible indicative signals of the probe.

In addition, as shown in FIG. 1, the tactile probe may be further provided at its foremost end with a contact sleeve cap 8 which is adhesively attached to the contact sleeve 1 integrally, with the edge of the polymeric elastomer 5 optionally adhesively affixed between the contact sleeve cap 8 and the contact sleeve 1. When the tactile probe hits an obstacle, the contact sleeve cap 8 will move in synchronization with the contact sleeve 1. The contact sleeve cap 8 can accommodate the leading end of the central column 7 as well as the polymeric elastomer 5 to provide them with protection.

Figure 9:
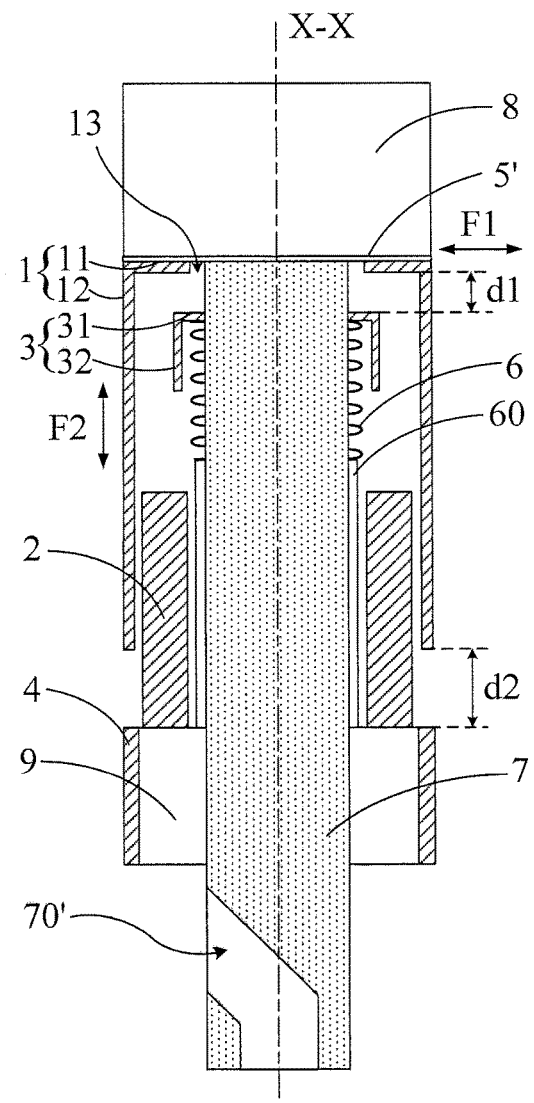
FIG. 9 schematically shows an opening formed in a side surface of an interventional catheter.

Depending on the design requirements, the central column 7 may be either solid or hollow. As shown in FIGS. 1 to 6, the central column 7 is hollow, and the polymeric elastomer 5 accordingly has a central opening, with the contact sleeve cap 8 optionally also having an opening (not shown) at the leading end. The hollow central column enables an opening 70 of the interventional catheter to be arranged at the front end, through which an interventional device can be inserted or withdrawn and a liquid medicament can be released, almost without any damage to the blood vessel wall. In case of a solid central column being applied, a leading end of the interventional catheter is covered by the solid central column, and the opening 70' of the interventional catheter can be arranged on its side surface (see FIG. 9). In this case, neither the polymeric elastomer 5' nor the leading end of the contact sleeve cap 8 is necessary to have an opening.

Figure 8A:
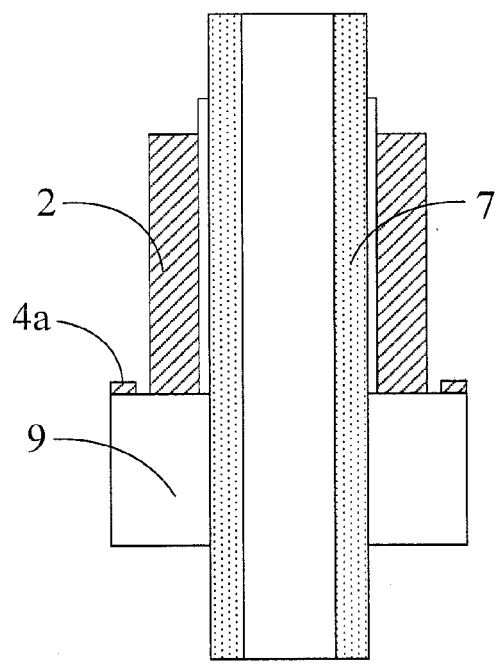
FIGS. 8A and 8B show variants of a threshold alert electrode.
Figure 8B:
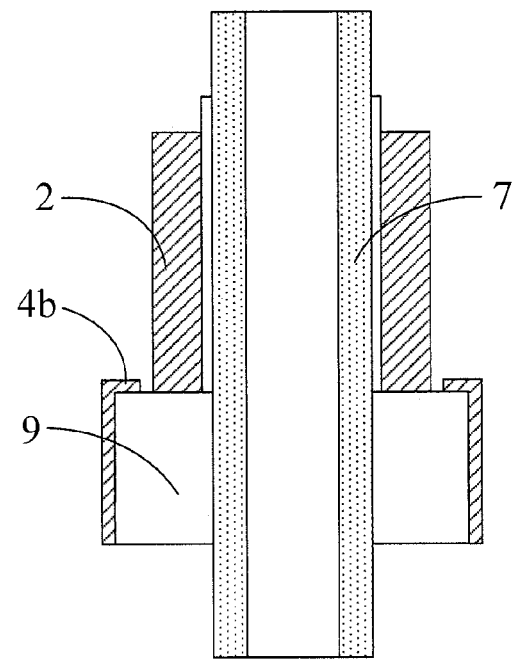

While it has been illustrated in FIGS. 1 to 7 that there is a small gap between the lateral electrodes 2 and the central column 7 or between the lateral electrodes 2 and the spring seat 60, in practical fabrication, the lateral electrodes 2 may be made in a close fit to the central column 7 or to the spring seat 60 (see FIGS. 8A and 8B). Since the lateral electrodes 2 are rigid metal components, the central column 7 also possesses a certain rigidity and therefore will not be bent under an external force. This ensures that the side wall 12 of the contact sleeve can always be brought into contact with the threshold alert electrode 4. For the solid central column, lower requirements are applicable to its non-deformability under an external force than the hollow central column.

As variants of this embodiment, the threshold alert electrode 4 may also be a sheet-like electrode 4*a* arranged on the leading surface of the lateral-electrode base 9 as shown in FIG. 8A or may be an electrode 4*b* arranged on both the leading and side surfaces of the lateral-electrode base 9 as shown in FIG. 8B, or have any appropriate shape which ensures that the threshold alert electrode 4 is not in contact with the lateral electrodes 2 or separated therefrom by an insulating layer, and that the threshold alert electrode 4 is axially aligned with the side wall 12 of the contact sleeve.

Embodiment 2

Figure 10:
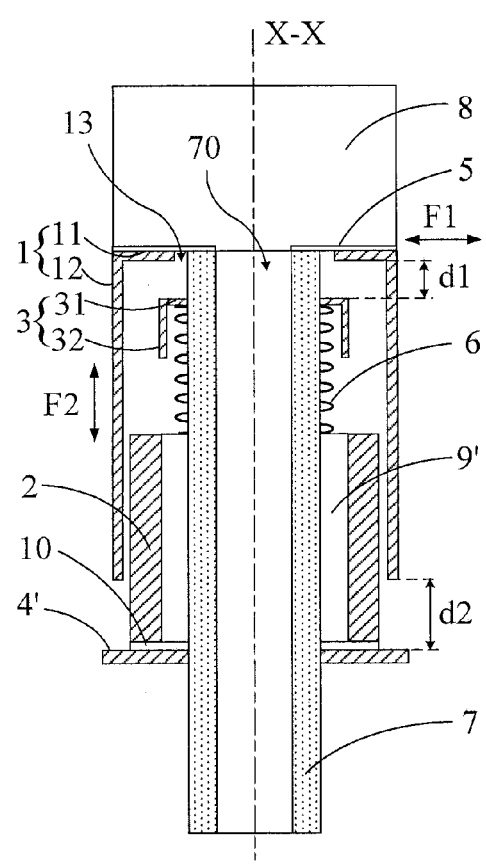
FIG. 10 is a schematic cross-sectional view of a tactile probe according to a second embodiment of the present invention.

A tactile probe according to this embodiment is shown in FIG. 10, in which the same reference numerals are used to identify the same elements as in Embodiment 1. The tactile probe according to this embodiment includes: a central column 7 extending along a longitudinal axis X-X; a contact sleeve 1 connected to the central column 7 via a polymeric elastomer 5; a plurality of lateral electrodes 2 evenly distributed around the central column 7; a top electrode 3 attached to the central column 7 through a spring 6; and a threshold alert electrode 4' fixed on a lateral-electrode base 9'. Differing from Embodiment 1, in this embodiment, the plurality of lateral electrodes 2 are evenly disposed on the circumference of a wall of the lateral-electrode base 9', and the threshold alert electrode 4' is fixed on the bottom of the lateral-electrode base 9' and radially extends outward so that the early-warning electrode 4' at least partially faces toward a trailing end of the annular side wall 12 of the contact sleeve 1 and is aligned therewith.

According to this embodiment, the probe has a smaller longitudinal (axial) length and is thus more compact in structure, with a trailing end of the spring 6 enabled to be directly attached to the lateral-electrode base 9', eliminating the use of the spring seat 60 of FIG. 1. In order for the lateral electrodes 2 to be electrically isolated from the threshold alert electrode 4' to prevent signal crosstalk, in this embodiment, an additional insulating layer 10 is disposed between the lateral electrodes 2 and the threshold alert electrode 4'. Further, the tactile probe may also include a contact sleeve cap 8 that is adhesively attached to the contact sleeve 1 into an integral part.

The tactile probe according to this embodiment operates in a similar way to that of Embodiment 1. The contact sleeve 1 serves as a signal input device, and the lateral electrodes 2, the top electrode 3 and the threshold alert electrode 4' each as a signal generator. As shown in FIG. 10, in an initial configuration in which the contact sleeve 1 is not subject to any external force, the axial distance from the leading surface 31 of the top electrode 3 to the top portion 11 of the contact sleeve is d1, and the axial distance from the threshold alert electrode 4' to the side wall 12 of the contact sleeve is d2. In case of the contact sleeve 1 hitting an obstacle straight ahead of it, the contact sleeve 1 will move backward along the axis X-X under the effect of a force exerted by the obstacle. Upon it having moved a distance of d1, the top portion 11 of the contact sleeve comes into contact with the leading surface 31 of the top electrode 3, closing a circuit which causes the top electrode 3 to output a signal indicative of the touch. If the contact sleeve 1 continues moving backward along the axis X-X under the force from straight ahead, the spring 6 will be compressed and drive the top electrode 3 to also move backward with the contact sleeve 1. Upon it having moved a distance of d2, the side wall 12 of the contact sleeve will come into contact with the threshold alert electrode 4', thereby closing a circuit which causes the threshold alert electrode 4' to output a warning signal indicating that the probe is being subject to a threshold pressure and further advancing of the interventional catheter should be stopped. In case of the contact sleeve 1 being subject to a pressure from obliquely ahead, in addition to the backward movement along the axis X-X, the contact sleeve 1 will also move radially so that when it radially comes into contact with one or two of the lateral electrodes 2, the corresponding circuit(s) will be closed and the lateral electrode(s) 2 will generate signal(s) indicating the lateral contacting.

Embodiment 3

A tactile probe according to this embodiment is shown in FIGS. 11 to 15, in which the same reference numerals are used to identify the same elements as in Embodiment 1. The tactile probe according to this embodiment includes: a central column 7 extending along a longitudinal axis X-X; a contact sleeve 1' connected to a leading end of the central column 7 via a polymeric elastomer 5; a lateral-electrode base 9 that is connected to the central column 7 by a spring 6 and is movable axially relative to the central column 7; a plurality of lateral electrodes 2 that are evenly distributed around the central column 7 and fixed on a leading surface of the lateral-electrode base 9; a top electrode 3' disposed on the lateral-electrode base 9; and a threshold alert electrode 4 fixed on an anchoring member 40 and disposed behind the top electrode 3'.

Different from Embodiment 1, in this embodiment, the contact sleeve 1' only has the annular side wall of FIG. 1 but not the top portion 11, and the top electrode 3' is an annular electrode that is disposed behind the contact sleeve 1' and over the circumference of the lateral-electrode base 9 and is axially aligned with the contact sleeve F. Additionally, compared to Embodiment 1, the third embodiment further includes an anchoring member 40 having a substantially U-shaped cross-section, and the spring 6 has its one end fixed to the bottom of the lateral-electrode base 9 and the other end anchored in the U-shaped anchoring member 40. The threshold alert electrode 4 is an annular electrode disposed/surrounding the anchoring member 40 and the threshold alert electrode 4 is axially aligned with the top electrode 3'.

Figure 11:
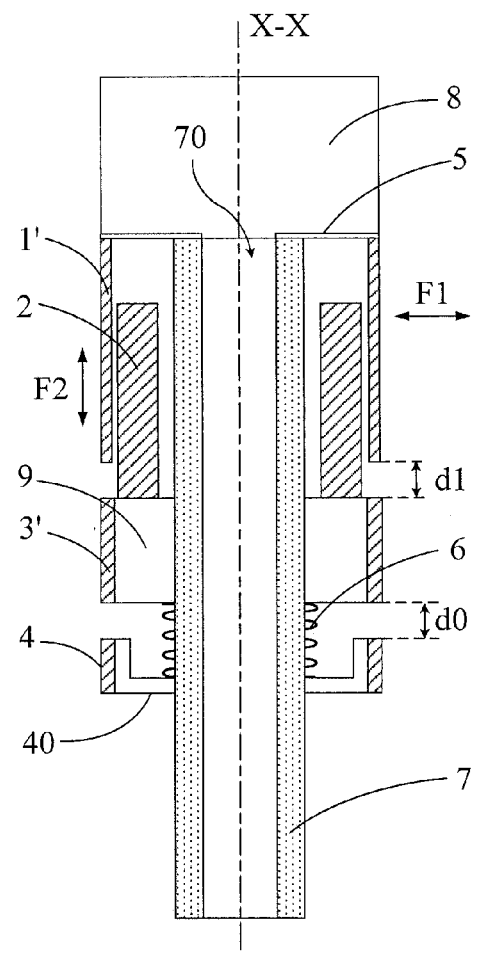
FIGS. 11 to 15 are schematic cross-sectional views of a tactile probe according to a third embodiment of the present invention.
Figure 12:
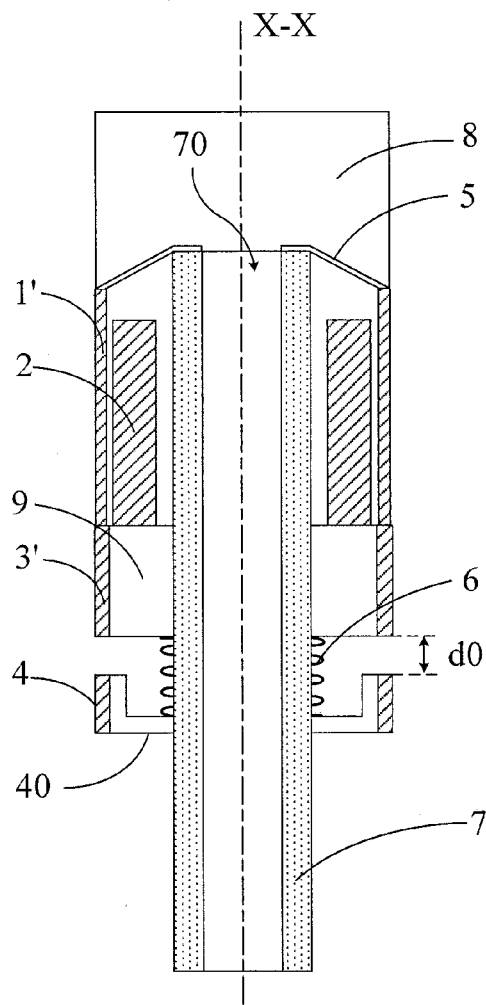
Figure 13:
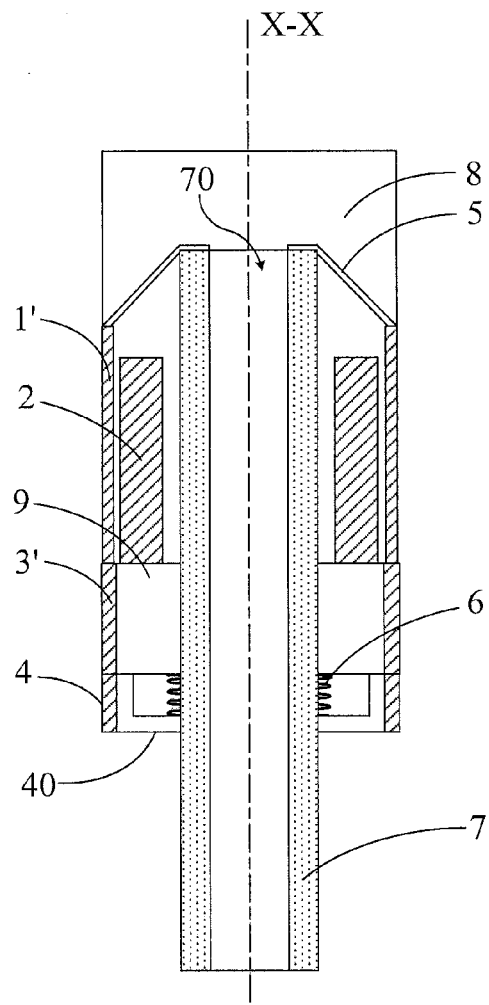

The tactile probe according to this embodiment works in a similar way to that of Embodiment 1. The contact sleeve 1' serves as a signal input device, and the lateral electrodes 2, the top electrode 3' and the threshold alert electrode 4 each as a signal generator. As shown in FIG. 11, in an initial configuration in which the contact sleeve 1' is not subject to any external force, the axial distance from the bottom of the contact sleeve 1' to the top of the top electrode 3' is d1, and the axial distance from the bottom of the top electrode 3' to the threshold alert electrode 4 is d0. When the contact sleeve 1' hits an obstacle straight ahead of it, the contact sleeve 1' will move backward along the axis X-X, i.e., toward the top electrode 3', under the effect of a force exerted by the obstacle. Upon it having moved a distance of d1, as shown in FIG. 12, the bottom of the contact sleeve 1' comes into contact with the top of the electrode 3', closing a circuit which causes the top electrode 3' to output a signal indicative of the contact. If the contact sleeve 1' continues moving backward along the axis X-X under the force from straight ahead, the bottom of the contact sleeve 1' will exert a backward force on the top electrode 3' and on the lateral-electrode base 9 whereon the top electrode 3' is fixed, so that the spring 6 is compressed and hence drives the top electrode 3' to also move backward together with the lateral-electrode base 9 and the plurality of lateral electrodes 2 fixed on the leading surface of the lateral-electrode base 9. Upon it having further moved a distance of d0 so that d1+d0, which corresponds to d2 of Embodiments 1 or 2, reaches a threshold, as shown in FIG. 13, the bottom of the top electrode 3' comes into contact with the threshold alert electrode 4, thereby enabling an indirectly contact between the contact sleeve 1' and the threshold alert electrode 4. As the contact sleeve 1', the top electrode 3' and the threshold alert electrode 4 are all conductive, a corresponding circuit is closed so that concurrently with the top electrode 3' outputting a signal indicating that it is being in contact, the threshold alert electrode 4 also output a warning signal indicating that the probe is being subject to a threshold pressure and further advancing of the interventional catheter should be stopped. The U-shaped cross section of the anchoring member 40 offers the advantage that the leading surface of the anchoring member 40 defines a recess in which the spring 6 can be received, thus allowing the top electrode 3' to take contact with the threshold alert electrode 4.

Figures 14, 15:
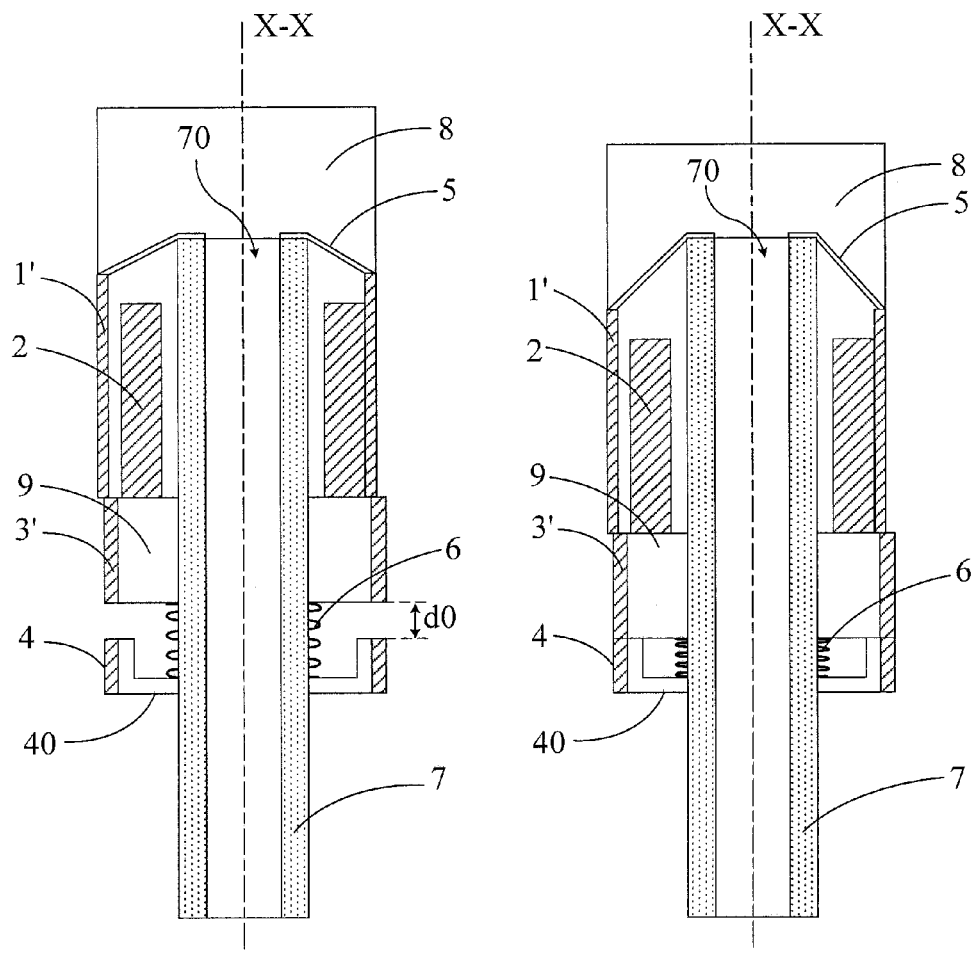

While the probe has been illustrated in FIGS. 12 and 13 as moving backward under a pressure from straight ahead, it will be readily appreciated by those skilled in the art that a pressure from obliquely ahead acting on the probe that consists of an axial component and a radial component will drive also radial movement of the contact sleeve 1' in addition to its backward movement along the axis X-X, so that when it radially comes into contact with one or two of the lateral electrodes 2, the lateral electrode(s) will also generate signal(s) indicative of the lateral contacting. FIGS. 14 and 15 show, under the effect of a pressure from right ahead, a schematic of the contact sleeve 1' coming into contact with the top electrode 3' and the lateral electrode(s) 2 and a schematic of the contact sleeve 1' forming a closed circuit together with the top electrode 3', the lateral electrode(s) 2 and the threshold alert electrode 4, respectively.

In addition, the tactile probe may further include a contact sleeve cap 8 disposed at its foremost end. The central column 7 may be either hollow or solid. The threshold alert electrode 4 may be a sheet-like electrode 4a as shown in FIG. 8A, or may be an electrode 4b having the shape as shown in FIG. 8B or any other suitable shape.

Embodiment 4

Figure 16:
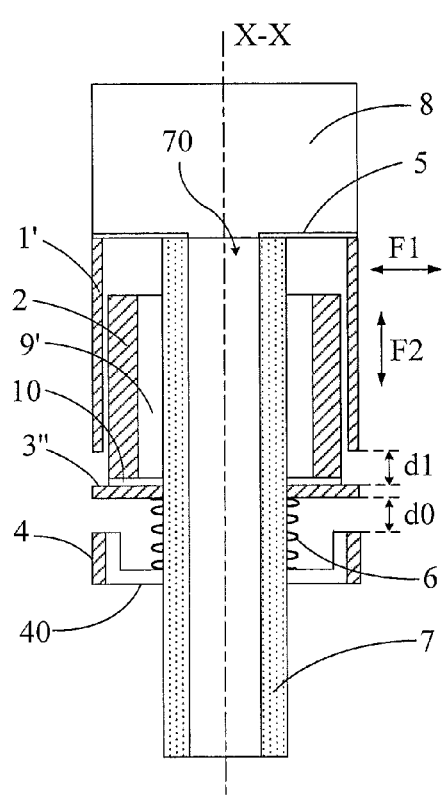
FIG. 16 is a schematic cross-sectional view of a tactile probe according to a fourth embodiment of the present invention.

A tactile probe according to this embodiment is shown in FIG. 16, in which the same reference numerals are used to identify the same elements as in Embodiment 3. The tactile probe according to this embodiment includes: a central column 7 extending along a longitudinal axis X-X; a contact sleeve 1' connected to a leading end of the central column 7 via a polymeric elastomer 5; a lateral-electrode base 9'; a plurality of lateral electrodes 2 that are evenly distributed around the central column 7 and fixed to the lateral-electrode base 9'; a top electrode 3" disposed on the bottom of the lateral-electrode base 9' and connected to the central column 7 by a spring 6; and a threshold alert electrode 4 fixed on an anchoring member 40 and disposed behind the top electrode 3". Different from Embodiment 3, in this embodiment, the plurality of lateral electrodes 2 are evenly disposed on the circumference of a wall of the lateral-electrode base 9', and the top electrode 3" is fixed on the bottom of the lateral-electrode base 9' and radially extends outward so that at least part of the leading surface of the top electrode 3" faces toward a trailing end of the annular side wall of the contact sleeve 1' and is aligned therewith, and that at least part of the trailing surface of the top electrode 3" faces toward the threshold alert electrode 4 and is aligned with the threshold alert electrode.

According to this embodiment, the probe has a smaller longitudinal (axial) length and is thus more compact in structure. In order for the lateral electrodes 2 to be electrically isolated from the top electrode 3" to prevent signal crosstalk, in this embodiment, an additional insulating layer 10 is disposed between the lateral electrodes 2 and the top electrode 3". Further, the tactile probe may also include a contact sleeve cap 8 that is adhesively attached to the contact sleeve 1' into an integral part.

The tactile probe according to this embodiment operates in a similar way to that of Embodiment 3. The contact sleeve 1' serves as a signal input device, and the lateral electrodes 2, the top electrode 3" and the threshold alert electrode 4 each as a signal generator. As shown in FIG. 16, in an initial configuration in which the contact sleeve 1' is not subject to any external force, the axial distance from the leading surface of the top electrode 3" to the bottom of the contact sleeve 1' is d1, and the axial distance from the trailing surface of the top electrode 3" to threshold alert electrode 4 is d0. When the contact sleeve 1' hits an obstacle straight ahead of it, the contact sleeve 1' will move backward along the axis X-X, i.e., toward the top electrode 3", under the effect of a force exerted by the obstacle. Upon it having moved a distance of d1, the bottom of the contact sleeve 1' comes into contact with the leading surface of the top electrode 3", thereby closing a circuit which causes the top electrode 3" to output a signal indicative of the touch. If the contact sleeve 1' continues moving backward along the axis X-X under the force from straight ahead, the bottom of the contact sleeve 1' will exert a backward force on the top electrode 3", so that the spring 6 is compressed and hence drives the top electrode 3" to also move backward together with the lateral-electrode base 9' and the plurality of lateral electrodes 2 fixed on the side surface of the lateral-electrode base 9'. Upon it having further moved a distance of d0 so that d1+d0, which corresponds to d2 of Embodiments 1 or 2, reaches a threshold, the trailing surface of the top electrode 3" comes into contact with the threshold alert electrode 4, thereby enabling an indirectly contact between the contact sleeve 1' and the threshold alert electrode 4. As the contact sleeve 1', the top electrode 3" and the threshold alert electrode 4 are all conductive, a corresponding circuit is closed so that concurrently with the top electrode 3" outputting a signal indicating that it is being in contact, the threshold alert electrode 4 also output a warning signal indicating that the probe is being subject to a threshold pressure and further advancing of the interventional catheter should be stopped. In case of the contact sleeve 1' being subject to a pressure from obliquely ahead, in addition to the backward movement along the axis X-X, the contact sleeve 1' will also move radially so that when it radially comes into contact with one or two of the lateral electrodes 2, the corresponding circuit(s) will be closed and the lateral electrode(s) 2 will generate signal(s) indicating the contacting.

Preferably, in this embodiment, the anchoring member 40 is also a U-shaped member which defines a space for accommodating the spring 6 to enable a contact between the top electrode 3" and the threshold alert electrode 4.

Figure 17:
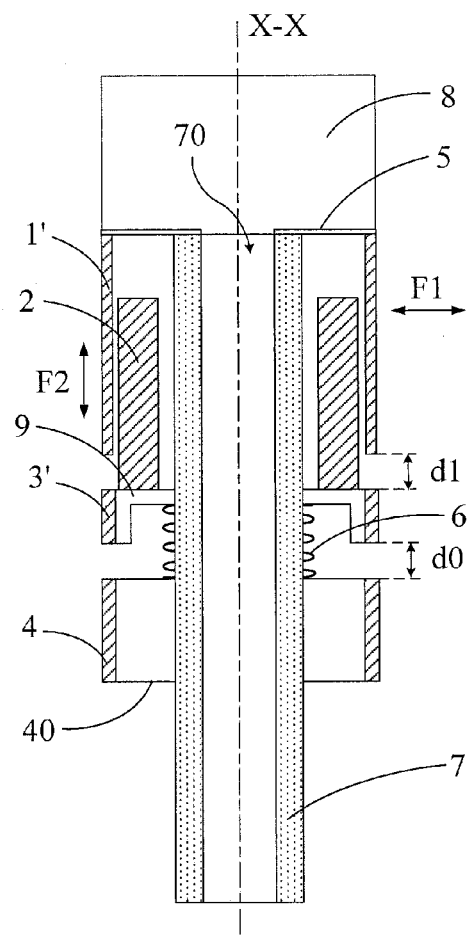
FIGS. 17 and 18 show variants of the third embodiment of the present invention.

In addition, as a variant of Embodiment 3, as shown in FIG. 17, the lateral-electrode base 9 may be a structure having an inverse U-shaped cross section and defining a recess at its bottom. The plurality of lateral electrodes 2 are arranged on the leading surface of the lateral-electrode base 9, with the top electrode 3' disposed on the circumference of the lateral-electrode base 9. One end of the spring 6 is fixed in the bottom recess of the lateral-electrode base 9, and the other end is fixed on the anchoring member 40. This structure also can provide a space for accommodating the spring 6, i.e., the space on the bottom of the lateral-electrode base 9. In this case, without specific limitations, the anchoring member 40 may have a rectangular or U-shaped cross section, and the threshold alert electrode 4 may be either an annulus (as shown) or a sheet.

Figure 18:
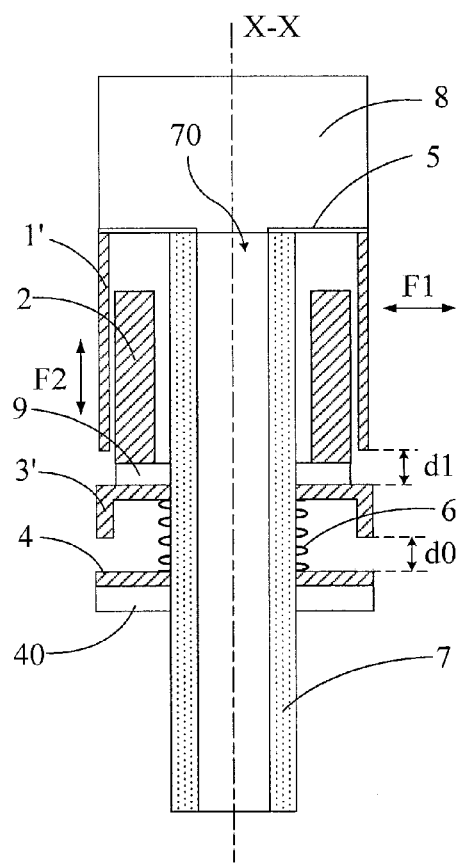

As another variant of Embodiment 3, as shown in FIG. 18, the top electrode 3' may be a structure having a substantially inverse U-shaped cross section and defining a recess at its bottom. The top electrode 3' is arranged on a trailing surface of the lateral-electrode base 9, with the plurality of lateral electrodes 2 disposed on the leading surface of the lateral-electrode base 9. One end of the spring 6 is secured in the bottom recess of the top electrode 3', and the other end is fixed to the anchoring member 40. The spring 6 may be formed of an insulating elastic material or a metal. In the case of the spring 6 being formed of a metal, an insulating layer for electrical isolation is further necessarily arranged between the end of the spring 6 and the top electrode 3'. This structure also can provide a space for receiving the spring 6, i.e., the space on the bottom of the top electrode 3'. In this case, without specific limitations, the anchoring member 40 may have a rectangular or U-shaped cross section, and the threshold alert electrode 4 may be either an annulus or a sheet (shown as a sheet in this figure). In this variant, with similarity to the case of the top electrode 3', when the threshold alert electrode 4 is shaped as a sheet-like electrode, the spring 6 may be formed of an insulating elastic material, or the spring 6 may be formed of a metal with an insulating layer for electrical isolation further arranged between the other end of the spring 6 and the threshold alert electrode 4.

Figure 19:
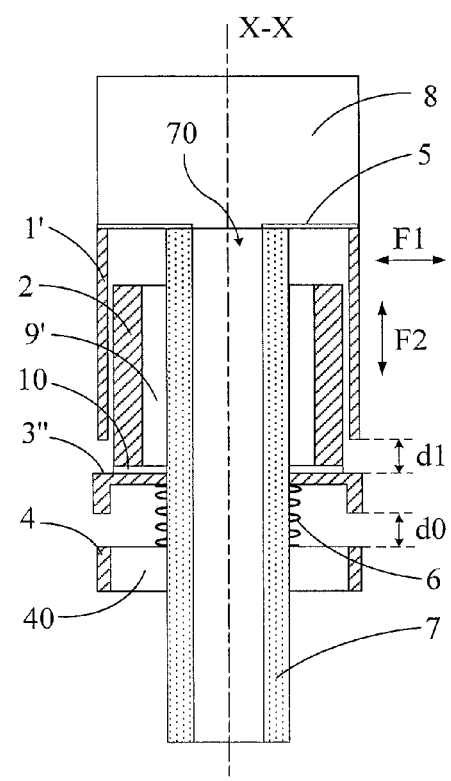
FIG. 19 shows a variant of the fourth embodiment of the present invention.

Furthermore, as a variant of Embodiment 4, as shown in FIG. 19, the top electrode 3" may be a structure having a substantially inverse U-shaped cross section and defining a recess at its bottom. The top electrode 3" is arranged on a trailing surface of the lateral-electrode base 9', with the plurality of lateral electrodes 2 disposed on the side surface of the lateral-electrode base 9', and the plurality of lateral electrodes 2 are separated from the top electrode 3" by an insulating layer 10. One end of the spring 6 is secured in the bottom recess of the top electrode 3", and the other end is fixed to the anchoring member 40. The spring 6 may be formed of an insulating elastic material or a metal. In the case of the spring 6 being formed of a metal, an insulating layer for electrical isolation is further necessarily arranged between the end of the spring 6 and the top electrode 3". This structure also can provide a space for receiving the spring 6, i.e., the space on the bottom of the top electrode 3". In this case, without specific limitations and with reference to FIGS. 17 and 18, the anchoring member 40 may have a rectangular or U-shaped cross section, and the threshold alert electrode 4 may be either an annulus or a sheet.

While several preferred embodiments of the present invention have been presented above, all equivalent changes and modification made within the scope of the appended claims are intended to fall within the scope thereof.

What is claimed is:

1. A tactile probe, comprising:
   an axially extending central column;
   a plurality of lateral electrodes evenly distributed around the central column;
   a conductive contact sleeve circumferentially surrounding the central column, the contact sleeve comprising a top portion and a side wall, the top portion connected by an elastomer to a leading end of the central column, the side wall having a first end in connection with the top portion and a second end circumferentially surrounding the plurality of lateral electrodes, the side wall spaced apart from each of the plurality of lateral electrodes by a radial gap;
   a top electrode connected to the central column and spaced from the top portion of the contact sleeve by a first axial distance; and
   an alert electrode fixed to the central column and positioned behind both the contact sleeve and the top electrode,
   wherein the contact sleeve is radially movable relative to the central column and is able to be electrically connected to at least one of the plurality of lateral electrodes to allow a lateral contact signal to be generated, and
   wherein the contact sleeve is axially movable relative to the central column such that in an event of the contact sleeve being axially displaced relative to the central column by the first axial distance, an electrical connection is established between the contact sleeve and the top electrode to generate a top contact signal, and in an event of the contact sleeve being axially displaced relative to the central column by a second axial distance that is greater than the first axial distance, an electrical connection is established between the contact sleeve and the alert electrode to generate a warning signal.

2. The tactile probe of claim 1, wherein the top electrode is moveably connected to the central column such that in an event of the contact sleeve being axially displaced relative to the central column by a distance that is greater than the first axial distance, the top electrode is able to axially move together with the contact sleeve with respect to the central column.

3. The tactile probe of claim 1, further comprising a lateral-electrode base fixed to the central column, wherein: the plurality of lateral electrodes and the alert electrode are both arranged on the lateral-electrode base; the alert electrode is at least partially axially aligned with the side wall of the contact sleeve; and the alert electrode is separated from the second end of the side wall of the contact sleeve by the second axial distance.

4. The tactile probe of claim 3, wherein the plurality of lateral electrodes are all arranged on a leading surface of the lateral-electrode base, and the alert electrode is an annular electrode that is disposed on a circumference of the lateral-electrode base and is axially aligned with the side wall of the contact sleeve.

5. The tactile probe of claim 3, wherein the plurality of lateral electrodes are all arranged on a leading surface of the lateral-electrode base, and the alert electrode is a sheet-like electrode that is disposed on the leading surface of the lateral-electrode base and is axially aligned with the side wall of the contact sleeve.

6. The tactile probe of claim 3, wherein the plurality of lateral electrodes are arranged on a circumference of the lateral-electrode base, and the alert electrode is arranged on a trailing surface of the lateral-electrode base and has an annular, radially extending portion aligned with the side wall of the contact sleeve.

7. A tactile probe, comprising:
an axially extending central column;
a plurality of lateral electrodes evenly distributed around the central column;
a substantially annular, conductive contact sleeve circumferentially surrounding the central column, the contact sleeve having a first end in connection with a leading end of the central column via an elastomer and a second end circumferentially surrounding the plurality of lateral electrodes, the contact sleeve spaced apart from each of the plurality of lateral electrodes by a radial gap;
a top electrode connected to the central column and spaced from the second end of the contact sleeve by a first axial distance; and
an alert electrode fixed to the central column and positioned behind both the contact sleeve and the top electrode,
wherein the contact sleeve is radially movable relative to the central column and is able to be electrically connected to at least one of the plurality of lateral electrodes to allow a lateral contact signal to be generated, and
wherein the contact sleeve is axially movable relative to the central column such that in an event of the contact sleeve being axially displaced relative to the central column by the first axial distance, an electrical connection is established between the contact sleeve and the top electrode to generate a top contact signal, and in an event of the contact sleeve being axially displaced relative to the central column by a second axial distance that is greater than the first axial distance, an electrical connection is established between the contact sleeve and the alert electrode to generate a warning signal.

8. The tactile probe of claim 7, further comprising:
a lateral-electrode base, wherein the plurality of lateral electrodes and the top electrode are all arranged on the lateral-electrode base, and one of the lateral-electrode base, the top electrode and the plurality of lateral electrodes is connected to the central column through an elastic component such that, in an event of the contact sleeve being axially displaced relative to the central column by a distance that is greater than the first axial distance, the lateral-electrode base, the top electrode and the plurality of lateral electrodes are all able to axially move together with the contact sleeve with respect to the central column; and
an anchoring member configured to fix the alert electrode to the central column,
wherein the top electrode is at least partially axially aligned with the alert electrode.

9. The tactile probe of claim 8, wherein: the plurality of lateral electrodes are all arranged on a leading surface of the lateral-electrode base; the lateral-electrode base is connected to the central column by the elastic component; and the top electrode is an annular electrode that is disposed on a circumference of the lateral-electrode base and is axially aligned with the side wall of the contact sleeve.

10. The tactile probe of claim 9, wherein the anchoring member has a U-shaped cross section, or the lateral-electrode base has an inverse U-shaped cross section.

11. The tactile probe of claim 8, wherein: the plurality of lateral electrodes are all arranged on a circumference of the lateral-electrode base; the top electrode is arranged on a trailing surface of the lateral-electrode base and has an annular, radially extending portion aligned with the second end of the contact sleeve; and the top electrode is connected to the central column by the elastic component.

12. The tactile probe of claim 11, wherein the anchoring member has a U-shaped cross section, or the top electrode has an inverse U-shaped cross section.

13. The tactile probe of claim 11, wherein the top electrode is separated from the elastic component by an insulating layer, or the elastic component is made of an insulating material.

14. The tactile probe of claim 9, wherein the alert electrode is an annular electrode that is arranged on a circumference of the anchoring member such that in an event of the contact sleeve being axially displaced relative to the central column by the second axial distance, an electrical connection is established between the second end of the contact sleeve and the alert electrode via the top electrode.

15. The tactile probe of claim 9, wherein the alert electrode is a sheet-like electrode that is arranged on a leading surface of the anchoring member such that in an event of the contact sleeve being axially displaced relative to the central column by the second axial distance, an electrical connection is established between the second end of the contact sleeve and the alert electrode via the top electrode.

16. The tactile probe of claim 1, wherein the top electrode and the alert electrode are both spaced apart from the plurality of lateral electrodes or separated from the plurality of lateral electrodes by an insulating layer.

17. The tactile probe of claim 1, wherein the contact sleeve further comprises a cap that is in connection with the top portion and is configured to accommodate the leading end of the central column and the elastomer, and wherein the central column is a hollow column, and a leading end of the cap of the contact sleeve defines an opening for a therapeutic device and/or a medicament to pass through.

18. The tactile probe of claim 7, wherein the contact sleeve further comprises a cap that is in connection with the top portion and is configured to accommodate the leading end of the central column and the elastomer, and wherein the central column is a hollow column, and a leading end of the cap of the contact sleeve defines an opening for a therapeutic device and/or a medicament to pass through.

19. The tactile probe of claim 1, wherein the contact sleeve further comprises a cap that is in connection with the top portion and is configured to accommodate the leading end of the central column and the elastomer, and wherein the central column is a solid column, and a side surface of a lower portion of the central column defines an opening for a therapeutic device and/or a medicament to pass through.

20. The tactile probe of claim 7, wherein the contact sleeve further comprises a cap that is in connection with the top portion and is configured to accommodate the leading end of the central column and the elastomer, and wherein the central column is a solid column, and a side surface of a lower portion of the central column defines an opening for a therapeutic device and/or a medicament to pass through.

* * * * *